United States Patent [19]

Provost et al.

[11] Patent Number: 5,278,149
[45] Date of Patent: Jan. 11, 1994

[54] METHOD OF PREPARING TOTAL PARENTERAL NUTRITION SOLUTIONS

[75] Inventors: Pamela S. Provost, Brighton; David F. Driscoll, West Bridgewater; Bruce R. Bistrian, Ipswich, all of Mass.

[73] Assignee: New England Deaconess Hospital Corporation, Boston, Mass.

[21] Appl. No.: 822,526

[22] Filed: Jan. 17, 1992

[51] Int. Cl.$^5$ .............. A61M 37/00; A61M 31/00; A61K 31/70; A61K 37/22
[52] U.S. Cl. .................. 514/23; 514/921; 514/938; 141/63; 141/114; 210/647; 604/50; 424/450
[58] Field of Search .......... 514/23, 938, 921; 141/63, 114; 210/647; 604/50; 424/450

[56] References Cited

U.S. PATENT DOCUMENTS

| | | | |
|---|---|---|---|
| 4,391,803 | 7/1983 | Fussi | 514/921 |
| 4,438,144 | 3/1984 | Blackburn | 424/319 |
| 4,548,817 | 10/1985 | Filley et al. | 424/717 |
| 4,550,022 | 10/1985 | Garabedian et al. | 424/717 |
| 4,688,577 | 8/1987 | Bro | 604/50 |
| 4,703,062 | 10/1987 | Blackburn et al. | 514/552 |
| 4,714,460 | 12/1987 | Calderon | 604/53 |
| 4,731,051 | 3/1988 | Fischell | 604/50 |
| 4,734,198 | 3/1988 | Harm et al. | 210/647 |
| 4,743,228 | 5/1988 | Butterfield | 604/50 |
| 4,752,618 | 6/1988 | Mascioli et al. | 514/549 |
| 4,810,726 | 3/1989 | Bistrian et al. | 514/552 |
| 4,820,731 | 4/1989 | Mascioli et al. | 514/549 |
| 4,846,792 | 7/1989 | Bobo et al. | 604/50 |
| 4,847,296 | 7/1989 | Babayan et al. | 514/552 |
| 4,871,768 | 10/1989 | Bistrian et al. | 514/547 |
| 4,880,014 | 11/1989 | Zarowitz et al. | 604/50 |
| 4,895,657 | 1/1990 | Polaschegg | 210/647 |
| 4,898,576 | 2/1990 | Philip | 604/50 |
| 4,922,975 | 5/1990 | Polaschegg | 114/114 |
| 4,941,875 | 7/1990 | Brennan | 604/83 |
| 4,952,606 | 8/1990 | Babayan et al. | 514/552 |
| 4,990,258 | 2/1991 | Bjare et al. | 210/647 |
| 5,116,316 | 5/1992 | Sertic et al. | 604/83 |

FOREIGN PATENT DOCUMENTS

WO9012080 10/1990 World Int. Prop. O. .

OTHER PUBLICATIONS

Driscoll, *Total Nutrient Admixtures in the Hospitalized Patient* Clinical Trends in Hospital Pharmacy vol. 5, No. 2, Second Quarter, 1991.
Driscoll, *Clinical Issues Regarding the Use of Total Nutrient Admixtures* 296 DICP, the Annals of Pharmacotherapy, 1990 Mar., vol. 24.
Brown, Quercia & Sigman, *Total Nutrient Admixture: A Review,* Review, vol. 10, No. 6.

*Primary Examiner*—Ronald W. Griffin
*Attorney, Agent, or Firm*—Lahive & Cockfield

[57] ABSTRACT

A method of preparing TPN solutions, which is particularly well adaptable to computerized control, has been developed. These methods can assist the pharmacist or physician in the preparation of three-in-one TPN solutions containing lipid, dextrose and amino acids. The method includes a series of criteria for concentrations of lipid, dextrose, amino acids, and ions as well as eliminating the possibility of certain deleterious interactions.

12 Claims, No Drawings

METHOD OF PREPARING TOTAL PARENTERAL NUTRITION SOLUTIONS

BACKGROUND OF THE INVENTION

The present invention relates to methods of making total parenteral nutrition (TPN) solutions. More particularly, the step-wise procedure for making TPN solutions which is disclosed herein guarantees that the solutions conform to acceptable standards of repeatability and physiologic compatibility. This method of forming TPN solutions is easily adapted to computerized control.

In the last few years, there has been a rapid expansion in the use of TPN solutions to treat hospitalized patients. In part, this expansion of TPN usage has been fueled by a series of discoveries which are leading to an optimization of TPN solutions for treatment of particular conditions. Nowhere is this more apparent than in the modification of the content of the fats used in TPN solutions. The traditional soybean or safflower oil used to provide the lipid content to TPN solutions is now being replaced, at least in part, by a variety of different lipids. These include omega-3 fatty acids (U.S. Pat. Nos. 4,752,618 and 4,871,731, both assigned to New England Deaconess Hospital Corporation), medium-chain triglycerides or MCT's (U.S. Pat. No. 4,528,197, assigned to KabiVitrum), structured lipids having both MCT and Omega-3 fatty acids on the same backbone (U.S. Pat. No. 4,871,768, assigned to New England Deaconess Hospital Corporation), kernel oils (U.S. Pat. No. 4,810,726, assigned to New England Deaconess Hospital Corporation), structured lipids containing dairy fats (U.S. Pat. No. 4,952,606, assigned to New England Deaconess Hospital Corporation), and structured lipids containing short-chain fatty acids (PCT Publication No. W090/12080, assigned to New England Deaconess Hospital Corporation). In addition, even the structure of the amino acids used in the parenteral nutrition solution have been modified. For certain uses, branched chain amino acids are preferable to straight chain amino acids (U.S. Pat. No. 4,438,144, assigned to Baxter Travenol Laboratories).

The rapid explosion of information concerning TPN solutions and what modifications must be made to the solutions when using each different type of fats and amino acids to achieve optimum results has made it particularly difficult for pharmacists and physicians to make sure the solutions are produced accurately. In addition, as more and different types of drugs are being delivered in conjunction with TPN solutions, determining compatibility of the drugs and a variety of ionic materials is more difficult for the physician and/or pharmacist ordering or formulating the TPN solution. Another factor which must be monitored is whether the various ionic materials affect the strength and stability of the lipid carrying emulsion itself. For example, if the concentration of ionic materials is too great or of the wrong type, the emulsion in the TPN solution may be destabilized or break down. Still another problem is making sure that the cumulative amounts of ions, drugs and other ingredients of the TPN solutions are monitored so that they do not exceed predetermined safety limits nor adversely affect the osmoticity of the solution. Similarly, the intravenous set used for delivery of the TPN solution must be of proper type for the particular TPN solution and it be changed, when necessary, because of any differences made in the TPN solution for a particular patient Accordingly, an object to the invention is to provide a method of preparing TPN solutions in a controlled manner such that there are no adverse drug or ionic interactions or emulsion destabilizing problems.

Another object to the invention is to provide a method of preparing TPN solutions so that mistakes which could be injurious to the patient by a pharmacist or physician are minimized.

A further object to the invention is to provide a computer control system for the manufacture of TPN solutions.

These and other objects and features of the invention will be apparent from the following detailed description.

SUMMARY OF THE INVENTION

The present invention features methods of making TPN solutions. These solutions can be made either manually by the pharmacist or under computer control. The method has a series of built-in tests or checks to ensure that the TPN solutions meet predetermined safety and other criteria.

While the methods of the invention have general applicability to TPN solutions, they are most applicable to what are called three-in-one solutions. These three-in-one TPN solutions include sufficient lipids, dextrose and amino acids so as to provide a nutrition program for a patient which can be used on a long term basis without deleterious side effects. These three-in-one solutions also normally include vitamins, and selected ionic materials such as dietary requirements of cations (e.g., Ca, Mg, K and Zn) and phosphate and chloride ions. In addition, these TPN solutions may be used as drug carriers for a variety of materials including heparin, steroid drugs (such as hydrocortisone), and cimetidine.

The TPN solutions are infused through an IV set, possibly with an in-line filter chamber, into the patient. Normally, the IV bags containing the TPN solution are changed several times a day or daily (while maintaining the same IV set), so that the cumulative amounts of each material on a per day or any predetermined infusion time basis, must be determined. The method also provides assistance in determining if the IV set should be changed.

The method of the invention for preparing a three-in-one total parenteral nutrition solution containing lipid, dextrose and amino acid components has multiple steps. These steps do not need to be carried out in the particular order set forth herein but it is preferable to follow this pattern. Normally, the first step is forming an emulsion of the lipid, dextrose, and amino acids, the concentrations of which must meet certain selected criteria. If conventional straight-chain amino acids are used as the sole amino acid source, the components of the TPN solution should meet the formulas:

$$2\% \leq A \leq 10\%$$

$$5\% \leq D \leq 25\%$$

$$2\% \leq L \leq 6\%$$

where A is the final concentration of amino acids, D is the final concentration of dextrose and L is the concentration of lipid in the final solution. However, if branched chain amino acids are used as some or all of the amino acids in the solution, the formulas which must be met are as follows:

$$2\% \leq A \leq 5\%$$

$$5\% \leq D \leq 15\%$$

$$2\% \leq L \leq 4\%$$

The concentration of the initial lipid solution used to make the final TPN solution is preferably 10-30%, and the total concentration of amino acids used to make the final TPN solution also must be not less than 2% and preferably is 3.5-15%. If branched chain amino acids are included, the concentration of amino acid used to make the final TPN solution should be 6.5-8.0% of the solution because of emulsion stability problems. Multivalent cations, or their derivatives, should be added to the emulsion in concentrations such that they do not destabilize (or break) the emulsion. These multivalent cations include iron (possibly in the form of iron dextran), zinc, calcium (possibly in the form of calcium gluconate), and magnesium. For example, if there are more than 10 mg/L of iron dextran or zinc, this may destabilize the emulsion. Similarly, concentrations greater than 20 mEq/L of divalent cations such as magnesium or calcium can disrupt the emulsion. In addition, materials such as HCl or albumin should not be used with fat (or lipid) containing TPN solutions as these may also destabilize the emulsion. Accordingly, if a predetermined amount of chloride (or other) salt is needed to treat a condition such as alkalosis, salts which do not destabilize the emulsion, such as NaCl or KCl should be used in lieu of HCl. These salts must also be compatible with other additives including acetate and steroid drugs such as prednisolone or hydrocortisone. If any drugs or ionic materials are added to the TPN solutions, the amounts added should be within predetermined safety limits. For example, calcium should be below 18 mEq/L while heparin should not exceed 12,000 units per day.

The method includes several steps which can be performed either by computer or manually. These steps include testing the compatibility of all drugs and additives incorporated into the emulsion for cross-reactivity, e.g., making sure that one additive does not diminish the effect of the others, as well as testing for safety reasons. In addition, the osmoticity of the final solution must be tested to make sure it is within acceptable limits, e.g., greater than 150 mOsm/L but less than 3500 mOsm/L. Patients who need TPN solutions are normally in some form of critical care and, as such, any variation of the osmoticity of solutions could cause shock or other physical problems.

The steps of this invention can be carried out, in whole or part, under computer control. Accordingly, the invention includes a computerized method for controlling the preparation of three-in-one TPN solutions. The computer controlled method has the steps of generating computer signals to an automatic mixing machine to form an emulsion of the lipid, dextrose and amino acids, whereby the concentration and compatibility criteria are the same as that previously described. The input of the various multivalent ions and other additives to the emulsion into the mixing chamber can be controlled by computer generated signals. This same type of computer control can also be used for adding any acid. If an acid is used, it should meet the same criteria as described previously, e.g., normally it should not be HCl. The compatibility of all materials added to make the TPN solution, such as multivitamins or drugs, can be determined from a computerized data base. This would eliminate the possibility of operator error in adding materials and it would allow easy updating so that the best information was available to the pharmacist or physician on the proper manner and materials with which to make the TPN solution. As the final step, the tonicity or osmoticity of the TPN solution can be tested, for example by using a computer controlled probe or merely by calculation.

These aspects of the invention will be more clearly evident from the following detailed description.

DETAILED DESCRIPTION

The present invention provides a method of preparing TPN solutions which provide optimum benefits to the patient and concurrently provide confirmation that nothing deleterious is included in the solution. The method further provides a series of checks that allow confirmation that the specific TPN solution is proper for the patient to whom it is to be given. This method can be carried out manually by a pharmacist or other trained professional, or it can be computerized. The method of making these TPN solutions can best be carried out using an automated mixing machine such as a Baxa Micro-Macro Compounder (Catalog No. 011), manufactured by Baxa Corporation. The Baxa Compounder can be controlled by computerized software which automates the process and confirms that each of the steps of the invention are carried out. This software has been tested by the inventors under the designation TPN-PC Plus Application Software—Parenteral Nutrition Formulation Program. This computerized system allow 5-50 units of TPN solution to be made per day under computer control.

The following, non-limiting example will better elucidate the method of the invention.

EXAMPLE

In this Example, a total of 3,800 orders were received for TPN solutions at a single hospital in a seven month period. All of these TPN solutions were made using the methods described herein. In over 700 of these orders, physician or pharmacist intervention was required (or was preferable) because the initial order, as placed, did not conform to the requisite standards for the method. In particular, the major problems were not properly scaling the amount of materials per bag or in multiple bag TPN, omitting drugs, and failure to properly conform to acceptable calcium-phosphate levels.

The method was carried out using a series of sequential steps and the automated mixer formulated the final TPN solution. The final concentration of amino acids and lipid in the TPN solution had to be at least 2%, so lipid and amino acid levels had to be confirmed. HCl and albumin could not be included in the TPN solutions that contained lipids because of the emulsion destabilizing effects. In addition, HCl could not be used in many other TPN solutions, even for treatment of alkalosis, because of the problem of interaction with acetate or steroid drugs. Similarly, concentrations of divalent cations and their derivatives were confirmed to be within acceptable levels. For example, the TPN solutions could not contain more than 10 mg/L of iron dextran or zinc nor more than 20 mEq/L of other divalent cations including Mg and Ca. Other ions, such as phosphate, potassium, and chloride, were added in amounts such that the solution had the proper tonicity. For example, if there were more than 18 mEq/L Ca or 40 mEq/L KCl, the solution would be improper in most circumstances and require pharmacist intervention.

All TPN solutions should include vitamins, for example a multivitamin such as MVI-12, and other necessary additives for nutrition purposes. The amount of any drug added to the TPN solution should not exceed the daily limits, even if the solution is cycled, e.g., infused at a rate so that it is consumed in less than a 24 hour period. Examples of drug limits include no more than 12,000 units of heparin per day nor more than 2400 mg of cimetidine per day. If multiple drugs or multiple bags are used, the compatibility of the drugs, and whether certain drugs should be deleted from any bags, can also be checked. Standard drugs for inclusion in the TPN solutions, in addition to the steroid drugs, are cimetidine, metoclopramide and heparin.

Another factor which is important in preparing the solutions is to make sure that if there are substantial changes from earlier TPN solutions, these modifications are accurate. Since, any large scale changes in dextrose or insulin concentration can be a potential for problems for the patient, any change orders were reason for intervention.

When selecting the amount of each of the three base components, e.g., lipid, amino acids, and dextrose, the following criteria were met. If solely straight chain amino acids were used, the final concentrations of each of the three components conformed to the following formula:

$$2\% \leq A \leq 10\%$$

$$5\% \leq D \leq 25\%$$

$$2\% \leq L \leq 6\%$$

If branched chain amino acids were used, the formula is as follows:

$$2\% \leq A \leq 5\%$$

$$5\% \leq D \leq 15\%$$

$$2\% \leq L \leq 4\%$$

In any case, both the final concentration of amino acids (A) and the concentration of lipids (L) exceeded 2% in the final solution. Preferably, the amino acid concentration in the solution used to make the solution was about 10%, with no more than 4% branched chain amino acids, and the lipid concentration was 10–30%. The dextrose concentration (D), as well as the concentration of amino acids and lipid, was selected as such that the final tonicity of the solution was >150 mOsm/L. A common TPN solution is made from components which are about 10% amino acids, 70% dextrose and 20% lipids.

Another advantage of using the methods of the invention are that it is relatively easy to confirm that the proper IV set or equipment is being used at the same time as the solutions are prepared. For example, if HCl was given in the preceeding 24 hour period and a three-in-one solution including fat is presently ordered (or vice-a-versa), the IV set should be changed because of potential deleterious interactions from residual solutions. Similarly, different sized filters are used for fat-containing and non-fat-containing TPN solutions and only the appropriate filter should be used in the IV set. The computer controlled mixing device of the present invention can give indicator messages to require that these items be noted on any labels or orders for the TPN solutions.

By following these guidelines, the methods of making the TPN solutions are easily computerized. For example, the Baxa computer controlled mixer previously described uses software which includes an instruction set that meets the foregoing requirements. If other mixers are used, the computer control can be handled with a PC or other small computer, but a mixing device which incorporates computer control is advantageous.

Those skilled in the art may determine other steps or additions to the described TPN solutions without changing the basic methods of manufacture described herein. Such other modifications or procedures are intended to be encompassed within the following claims.

What is claimed is:

1. A method of controlling the preparation of a three-in-one total parenteral nutrition solution containing lipid, dextrose, and amino acid components to ensure that said solution meets safety and stability criteria necessary for physiological compatibility and storage requirements comprising the steps of:
1) forming an emulsion of said lipid, said dextrose and said amino acids, the concentrations of each component being selected such that the following tests are met:
   a) if straight chain amino acids are used, $$2\% \leq A \leq 10\%$$

$$5\% \leq D \leq 25\%$$

$$2\% \leq L \leq 6\%; \text{ and}$$

b) if branched chain amino acids are used, $$2\% \leq A \leq 5\%$$

$$5\% \leq D \leq 15\%$$

$$2\% \leq L \leq 4\%; \text{ and}$$

where A is the concentration of amino acids, D is the concentration of dextrose, and L is the concentration of lipid;
2) adding multivalent cations, or their derivatives, in concentrations that do not destabilize said emulsion;
3) adding a salt, if needed, to achieve physiological alkalinization of said emulsion without destabilization, said salt being selected from the group consisting of salts compatible with lipids, steroid drugs and acetate;
4) adding any other ionic materials and drugs to be incorporated in said emulsion in amounts such that the final concentrations in said emulsion do not exceed physiological safety limits;
5) confirming the compatibility of all drugs and additives incorporated into said emulsion; and
6) testing the osmoticity of said emulsion to meet physiologically compatible osmoticity limits.

2. The method of claim 1 wherein said amino acids are solely straight chain amino acids, said adding step comprising adding said amino acids in the form of solution having 3.5–15% amino acids.

3. The method of claim 1 wherein said amino acids comprise branched chain amino acids, said adding step comprising adding branched chain amino acids in the form of solutions having 6.5-8.0% amino acids.

4. The method of claim 1 wherein said adding step comprises adding lipids in the form of emulsions having 10-30% lipids.

5. The method of claim 1 wherein said multivalent cations or their derivatives, are selected from the group consisting of iron ions, iron dextran, calcium ion, zinc ions, calcium gluconate, magnesium ion, and mixtures thereof.

6. The method of claim 1 wherein said step of adding drugs comprises adding drugs selected from the group consisting of steroid drugs, heparin, cimetidine, metoclopramide and mixtures thereof.

7. A computerized method of controlling the preparation of a three-in-one total parenteral nutrition solution containing lipid, dextrose, and amino acid components to ensure that said solution meets safety and stability criteria necessary for physiological compatibility and storage requirements comprising the steps of:

1) generating computer signals to an automatic mixing machine to form an emulsion of said lipid, said dextrose and said amino acids, the concentrations of each component being selected such that the following criteria are met:

a) if straight chain amino acids are used, $$2\% \leq A \leq 10$$

$$5\% \leq D \leq 25\%$$

$$2 \leq L \leq 6\%; \text{ and}$$

b) if branched chain amino acids are used, $$2\% \leq A \leq 5\%$$

$$5\% \leq D \leq 15\%$$

$$2\% \leq L \leq 4\%; \text{ and}$$

where A is the final concentration of amino acids, D is the final concentration of dextrose, and L is the final concentration of lipid;

2) generating computer signals to input devices on said mixing machine to control the addition of multivalent cations, or their derivatives, such that said multivalent cations, or their derivatives, are added in concentrations that do not destabilize said emulsion;

3) computer controlling the addition of a selected salt, if needed, to achieve a clinical response from said emulsion, said salt being selected from the group consisting of salts compatible with lipids, steroid drugs and acetate;

4) computer controlling the amounts added of any other ionic materials and drugs to be incorporated in said emulsion such that the final concentrations of said ionic materials and drugs in said emulsion do not exceed physiological safety limits;

5) confirming the compatibility of all drugs and additives to be incorporated into said emulsion; and 6) testing the osmoticity of said emulsion to meet physiologically compatible osmoticity limits.

8. The method of claim 7 wherein said amino acids are solely straight chain amino acids, said adding step comprising adding said amino acids in the form of solutions having 3.5-15% amino acids.

9. The method of claim 7 wherein said amino acids comprise branched chain amino acids, said adding step comprising adding branched chain amino acids in the form of solutions having 6.5-8.0% amino acids.

10. The method of claim 7 wherein said adding step comprises adding lipids in the form of emulsions having 10-30% lipids.

11. The method of claim 7 wherein said multivalent cations or their derivatives, are selected from the group consisting of iron ions, iron dextran, calcium ion, zinc ions, calcium gluconate, magnesium ion, and mixtures thereof.

12. The method of claim 7 wherein said step of adding drugs comprises adding drugs selected from the group consisting of steroid drugs, heparin, cimetidine, metoclopramide and mixtures thereof.

* * * * *